US009725370B2

(12) United States Patent
Jahns

(10) Patent No.: US 9,725,370 B2
(45) Date of Patent: Aug. 8, 2017

(54) WHITENING COMPOSITION FOR SELECTIVELY TREATING THE SURFACE OF DENTAL CERAMIC AND RELATED METHODS

(71) Applicant: 3M INNOVATIVE PROPERTIES COMPANY, Saint Paul, MN (US)

(72) Inventor: Michael Jahns, Gilching (DE)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 517 days.

(21) Appl. No.: 14/351,964

(22) PCT Filed: Oct. 29, 2012

(86) PCT No.: PCT/US2012/062361
§ 371 (c)(1),
(2) Date: Apr. 15, 2014

(87) PCT Pub. No.: WO2013/070451
PCT Pub. Date: May 16, 2013

(65) Prior Publication Data
US 2015/0336853 A1 Nov. 26, 2015

(30) Foreign Application Priority Data

Nov. 7, 2011 (EP) .................................... 11188005

(51) Int. Cl.
*A61C 13/08* (2006.01)
*C04B 41/45* (2006.01)
(Continued)

(52) U.S. Cl.
CPC ............ *C04B 41/4572* (2013.01); *A61C 5/70* (2017.02); *A61C 8/005* (2013.01); *A61C 13/01* (2013.01);
(Continued)

(58) Field of Classification Search
CPC . A61K 6/02; A61K 6/04; A61K 6/043; A61K 6/046
(Continued)

(56) References Cited

U.S. PATENT DOCUMENTS 6,709,694 B1   3/2004   Suttor
6,756,421 B1   6/2004   Todo
(Continued)

FOREIGN PATENT DOCUMENTS

EP   1177189   12/2005
EP   1961719   8/2008
(Continued)

OTHER PUBLICATIONS

Eschenbaum, "Thin films of proton conducting $SrZrO_3$-ceramics prepared by the sol-gel method", Solid State Ionics, 1995, vol. 77, pp. 222-225.
(Continued)

*Primary Examiner* — Ellen C Hammond
*Assistant Examiner* — Christina Negrellirodrigue

(57) ABSTRACT

The invention relates to a process of selectively treating parts of the surface of a porous dental ceramic comprising the steps of a) providing a composition and a porous dental ceramic having an outer surface, b) applying the composition to only a part of the outer surface of the porous dental ceramic, c) optionally drying the porous dental ceramic, and d) optionally firing the porous dental ceramic, wherein the composition comprises—a liquid being miscible with water, but not being water, —a whitening agent comprising nano-sized metal oxide particles, metal ion containing components or mixtures thereof which precipitate if the composition is adjusted to a pH above 5, —acid, complexing agent or mixture thereof. The invention also relates to a dental ceramic article obtainable by a process.

14 Claims, 1 Drawing Sheet

(51) Int. Cl.

| | |
|---|---|
| *C04B 41/50* | (2006.01) |
| *C04B 41/00* | (2006.01) |
| *A61C 8/00* | (2006.01) |
| *A61C 13/01* | (2006.01) |
| *B65D 81/32* | (2006.01) |
| *B65D 85/00* | (2006.01) |
| *C04B 41/85* | (2006.01) |
| *C04B 41/89* | (2006.01) |
| *C04B 41/52* | (2006.01) |
| *A61C 5/70* | (2017.01) |
| *C04B 111/00* | (2006.01) |
| *C04B 111/80* | (2006.01) |

(52) U.S. Cl.
CPC ............ *A61C 13/082* (2013.01); *B65D 81/32* (2013.01); *B65D 85/70* (2013.01); *C04B 41/009* (2013.01); *C04B 41/0072* (2013.01); *C04B 41/5072* (2013.01); *C04B 41/52* (2013.01); *C04B 41/85* (2013.01); *C04B 41/89* (2013.01); *C04B 2111/00836* (2013.01); *C04B 2111/80* (2013.01)

(58) Field of Classification Search
USPC ........................................... 433/199.1–212.1
See application file for complete search history.

(56) References Cited

U.S. PATENT DOCUMENTS

| | | | |
|---|---|---|---|
| 2002/0099053 A1 | 7/2002 | Gutmann | |
| 2005/0084823 A1* | 4/2005 | Foser ................... | A61C 13/09 |
| | | | 433/202.1 |
| 2006/0117989 A1 | 6/2006 | Hauptmann | |
| 2008/0070191 A1* | 3/2008 | Ricks .................. | A61C 13/083 |
| | | | 433/202.1 |
| 2012/0064490 A1* | 3/2012 | Rothbrust ............. | C04B 35/481 |
| | | | 433/199.1 |

FOREIGN PATENT DOCUMENTS

| | | |
|---|---|---|
| WO | WO 00-71724 | 11/2000 |
| WO | WO 2004-110959 | 12/2004 |
| WO | WO 2008-098157 | 8/2008 |
| WO | WO 2009-014903 | 1/2009 |
| WO | WO 2013-022612 | 2/2013 |
| WO | WO 2013-055432 | 4/2013 |

OTHER PUBLICATIONS

International Search Report for PCT International Application No. PCT/US2012/062361 mailed on Jan. 7, 2013, 3 pages.

* cited by examiner

WHITENING COMPOSITION FOR SELECTIVELY TREATING THE SURFACE OF DENTAL CERAMIC AND RELATED METHODS

CROSS REFERENCE TO RELATED APPLICATIONS

This application is a national stage filing under 35 U.S.C. 371 PCT/US 2012/062361, filed Oct. 29, 2012, which claims priority to European Application No. 11188005.0 filed Nov. 7, 2011, the disclosures of which are incorporated by reference in their entirety herein.

FIELD OF THE INVENTION

The invention relates to a process of selectively treating parts of the surface of a porous dental ceramic. The invention also relates to a composition which can be used in such a process, wherein the composition comprises a liquid and a whitening agent.

BACKGROUND OF THE INVENTION

A dental ceramic can be colored e.g. by incorporating pigments into the ceramic material from the very beginning or using metal salts containing solutions which are applied on the surface of a porous dental ceramic article with the aim to color the dental ceramic article in its entirety. Coloring solutions are described in a couple of documents:

WO 2004/110959 relates to a colouring solution for ceramic framework. The solution comprises a solvent (e.g. water), a metal salt and polyethylene glycol having a Mn in the range of 1.000 to 200.000.

WO 00/46168 A1 (corresponding to U.S. Pat. No. 6,709,694 B1) refers to colouring ceramics by way of ionic or complex-containing solutions containing defined concentrations of at least one salts or complexes of the rare earth elements or of the elements of the subgroups. The solution might contain additives like stabilizers, complex builders, pigments and beating additives.

WO 2008/098157 relates to a colouring solution for dental ceramic framework comprising a solvent, a colouring agent comprising metal ions, and a complexing agent, wherein the amount of complexing agent is sufficient to dissolve the colouring agent in the solvent.

WO 2009/014903 relates to a colouring solution for dental ceramic articles, the solution comprising a solvent and a colouring agent comprising rare earth element ions being present in the solution in an amount of at least about 0.05 mol/l solvent and transition ions being present in the solution in an amount of about 0.00001 to about 0.05 mol/l solvent.

J. Eschenbaum et al. describes in Solid State Ionics 77 (1995) 222-225 thin films or proton conducting $SrZrO_3$-ceramics prepared by the sol-gel method.

Sometimes, however, it is also desirable to use a whitening agent. Whitening agents are typically used to cover the metallic surface of a metallic dental framework in order to give the final dental restoration a more natural appearance. In certain cases, it can also be desirable to opacify e.g. the inner surface of a ceramic framework to cover discolourations of the tooth stump.

Compositions for whitening or opacifying dental metallic restorations are available in the market. Those compositions typically form a separate layer on the surface of the metallic framework and do not become part of the framework. These compositions often contain titania as a whitening pigment to achieve the desired whitening effect.

The present invention is intended to improve the known colouring and/or whitening processes.

SUMMARY OF THE INVENTION

In particular, it would be desirable to have a composition, which can be used to selectively treat specific parts of the surface of porous dental ceramic.

Moreover, it would be desirable if this can be done without a complete diffusion of the composition into the pores of pre-sintered or porous dental ceramic so that a defined application of the composition can be accomplished.

At least one of these objects can be achieve by providing a process of selectively treating parts of the surface of a porous dental ceramic comprising the steps of
 a) providing a composition and a porous dental ceramic having an outer and inner surface,
 b) applying the composition to only a part of the outer and/or inner surface of the porous dental ceramic,
 c) optionally drying the porous dental ceramic, and
 d) optionally firing the porous dental ceramic,
 wherein the composition comprises
  a liquid being miscible with water, but not being water,
  a whitening agent comprising nano-sized metal oxide particles, metal ion containing components or mixtures thereof which precipitate if the composition is adjusted to a pH above 5,
  an acid, complexing agent or mixture thereof.

According to a further aspect the invention relates to a composition comprising
 a liquid being miscible with water, but not being water,
 a whitening agent comprising nano-sized metal oxide particles, metal ion containing components or mixtures thereof which precipitate if the composition is adjusted to a pH above 5,
 an acid, complexing agent or mixture thereof.

In another aspect, the invention relates to a dental ceramic treated with the composition or obtainable by the process described in the present text.

In a further aspect, the invention relates to the use of the composition as described in the present text for selectively whitening the outer surface of a dental ceramic.

In a further aspect the invention relates to a kit of parts comprising at least one receptacle containing the composition as described in the present text and a receptacle containing a colouring liquid as described in the present text and optionally application and mixing appliances.

Unless defined differently, for this description the following terms shall have the given meaning:

A "liquid" is any substance which is able to solubilise, dissolve or disperse the whitening agent. The liquid should be sufficiently chemically stable if combined with the whitening agent. That is, the liquid shall not be decomposed by the other components present in the composition.

"Soluble" means that a component (solid) can be completely dissolved within a solvent. That is, the substance is able to form individual molecules (like glucose) or ions (like sodium chloride) or non-settling particles (like a sol) when dispersed in water at 23° C. The solution process, however, might take some time, e.g. stirring the composition over a couple of hours (e.g. 10 or 20 h) might be required.

More specifically, according to the invention a substance or composition is defined as "soluble", if less than about 10 wt.-% or less than about 5 wt.-% or less than about 2 wt.-% or less than about 1 wt.-% or less than about 0.1 wt.-% (with respect to the whole composition) of solid substance remains after the following procedure:
  a. 800 mg of substance and 8.0 g of solvent are placed into a centrifuge test tube of known weight.
  b. The test tube is closed and shaken for 60 minutes.
  c. The mixture is centrifuged with centrifugal acceleration (ac) of 9870 m/s$^2$ for 20 min.
  d. The supernatant liquid is decanted.
  e. The precipitate is re-suspended with 6 g solvent.
  f. The test tube is shaken for 60 min, centrifuged as described above, and the supernatant liquid decanted again.
  g. Steps e) and f) are repeated one time.
  h. The remaining precipitate is calcined for 12 h at 500° C. (+/−3.5° C.).
  i. After cooling to room temperature the dry weight of the sample is determined and used for calculating the soluble fraction.

A substance or composition is defined as "insoluble", if more than about 90 wt.-% or more than about 50 wt.-% or more than about 25 wt.-% or more than about 10 wt.-% (with respect to the whole composition) of substance remains unsolved after the procedure described above.

The term "water-miscible" or "miscible with water" means that a certain liquid is miscible with water at 23° C. at least to a high extend to provide a homogeneous solution, i.e. without phase separation. More specifically, the water-miscible liquid is defined as miscible with water if at least 10 g or at least 100 g or at least 500 g or at least 750 g or least 1000 g water-miscible liquid is soluble in 1000 g water without phase separation. Ideally, no phase separation occurs at ambient conditions independent from the mixing ratio (e.g. ethanol is miscible with water in all ratios).

The term "amount sufficient to dissolve" describes the amount of an agent needed to fully dissolve a certain substance in a certain solvent so that a storage stable composition can be obtained. The time needed to dissolve a substance is not particularly limited, however, the dissolution should occur within a reasonable time (e.g. within about 10 to about 48 h) using common equipment like mechanical stirrers and heaters.

A solution can be classified as "storage stable", if it remains stable over a considerable long period of time (at least about 4 weeks to more than about 12 months under ambient conditions). A storage stable solution typically does not show any visible (visible to the human eye) precipitation of the colouring agent during storage at ambient conditions (about 23° C., about 1013 mbar) and does not show decomposition of the solution or precipitation of single or multiple components.

"Non-water based" means that the major part (at least more than about 50 or more than about 60 or more than about 70 or more than about 80 or more than about 90 wt.-%) of the liquid components being present in the composition or solution is/are components being different from water.

A "whitening agent" is an agent, which is able to whiten the surface of a dental ceramic either right after treatment of the ceramic with the whitening agent or after conducting a firing step of the treated ceramic. The whitening effect typically goes along with an increase in opacity.

"Agglomeration" means the formation of a mass being comprised of particles. An example for an agglomeration is the formation of a precipitate of a chemical substance, which might be caused by the formation salt being insoluble or hardly soluble in a liquid or solvent. Another example for an agglomeration is the formation of aggregates from e.g. previously nano-sized particles, which might be caused by a disturbance of the stabilizing solvent environment. Exemplifying evidence for an agglomeration is the precipitation of a solid from a solution or liquid, or the clouding of the solution or liquid e.g. caused by a change of the pH value.

A "complexing agent" is any agent which is able to form complexes with the whitening agent.

A "complex", also known as coordination compound, in chemistry usually is used to describe molecules or ensembles formed by the combination of ligands and metal ions. Originally, a complex implied a reversible association of molecules, atoms, or ions through weak chemical bonds. As applied to coordination chemistry, this meaning has evolved. Some metal complexes are formed virtually irreversibly and many are bound together by bonds that are quite strong.

The ions or molecules surrounding the metal are called ligands. Ligands are generally bound to a metal ion by a coordinative bonding (donating electrons from a lone electron pair to the Lewis acidic metal center), and are thus said to be coordinated to the ion. Those ligands are referred to as "coordinating ligands".

Rare earth elements and/or of the subgroups of the rare earth elements include Ce, Pr, Nd, Sm, Eu, Gd, Tb, Dy, Ho, Er, Tm, Yb and Lu.

Transition metals comprise the metals listed in the columns of the Periodic Table of Elements starting with the elements Sc, Ti, V, Cr, Mn, Fe, Co, Ni, Cu and Zn and the metals listed below those elements.

Metals of the main groups comprise the metals listed in the main groups of the Periodic Table of Elements starting with the elements Li, Be, B, C, N, O, F and the metals listed below those elements.

A "particle" means a substance being a solid having a shape which can be geometrically determined. Particles can typically be analysed with respect to e.g. grain size or diameter.

The mean particle size of a powder can be obtained from the cumulative curve of the grain size distribution and is defined as the arithmetic average of the measured grain sizes of a certain powder mixture. Respective measurements can be done using commercially available granulometers (e.g. CILAS Laser Diffraction Particle Size Analysis Instrument).

A "powder" means a dry, bulk solid composed of a large number of very fine particles that may flow freely when shaken or tilted.

The term "dental ceramic" is to be understood as any ceramic which can be used in the dental field. In this respect, the dental ceramic shall have sufficient strength. Examples include inlays, onlays, veneers, crowns, abutments, bridges (including 2 parts, 3 parts, 4 parts, 5 parts or 6 parts bridges) and frameworks forming the support structure for a crown or bridge. The dental ceramic has usually a 3-dimensional inner and outer surface including convex and concave structures. Compared to other ceramic such as pottery or paving stones, the dental ceramic is small and filigree. The thickness of the dental ceramic can vary from very thin, e.g. at the edges and rims (below about 0.1 mm) to considerably thick, e.g. in the biting area (up to about 7 mm).

Typically, the dental ceramic of the invention comprises or essentially consists of a polycrystalline ceramic material comprising $Al_2O_3$ or Yttrium stabilized $ZrO_2$.

A dental ceramic is classified as "pre-sintered" if the dental ceramic has been treated with heat (temperature range from about 900 to about 1100° C.) for about 1 to about 3 h to such an extent that the raw breaking resistance of the dental ceramic measured according to the "punch on three ball test" ISO 6872 is within a range of about 15 to about 55 MPa or about 30 to about 50 MPa. A pre-sintered dental ceramic usually has a porous structure and its density (usually 3.0 g/cm³ for an Yttrium stabilized $ZrO_2$ ceramic) is less compared to a completely sintered dental ceramic framework (usually 6.1 g/cm³ for an Yttrium stabilized $ZrO_2$ ceramic).

A dental ceramic is classified as "absorbent" if the dental ceramic is able to absorb a certain amount of a solvent, comparable to a sponge. The amount of solvent which can be absorbed depends e.g. on the chemical nature of the dental ceramic framework, the viscosity of the solvent, the porosity and pore volume of the dental ceramic.

A "porous material" refers to a material comprising a partial volume that is formed by voids, pores, or cells in the technical field of ceramics. Accordingly an "open-celled" structure of a material sometimes is referred to as "open-porous" structure, and a "closed-celled" material structure sometimes is referred to as a "closed-porous" structure. It may also be found that instead of the term "cell" sometimes "pore" is used in this technical field. The material structure categories "open-celled" and "closed-celled" can be determined for different porosities measured at different material samples (e.g. using a mercury "Poremaster 60-GT" from Quantachrome Inc., USA) according to DIN 66133. A material having an open-celled or open-porous structure can be passed through by e.g. gases.

A dental ceramic can be characterized as "homogeneously coloured", if no colour spots can be identified with the human eye on the surface of the dental ceramic after the sintering process. More precisely, this can be proven e.g. using a commercially available Hunter Lab System or the system GretagMacbeth Colour i7. If desired, the homogeneity can be measured according to DIN 5033 Measurement of Colours; Parts 1-8 (Normvalenz-System, L*a*b*-Farbraum nach CIE, 1976); DIN 6174 Farbmetrische Bestimmung von Farbabständen bei Körperfarben nach der CIE-LAB-Formel; DIN 55981 (ISO 787-25) Farbabstandsbestimmung ΔE* using standard operating procedures according to the manufacturer's operation manual (Hunter Lab., Corp.) to determine the sample dimension, the calibration and measure procedure. Further hints to this measuring system can also be found in DE 100 52 203 A1 on page 3, line 56 to page 4, line 6 (corresponding to U.S. Pat. No. 6,756,421, column 4, lines 26 to 55).

By "machining" is meant milling, grinding, cutting, carving, or shaping a material by a machine. Milling is usually faster and more cost effective than grinding.

"Sintering" means making objects from a powder, by heating the material (typically below its melting point—solid state sintering) until its particles adhere to each other.

"Glass and/or glass ceramic material" means that the material comprises either a glass material alone or that the material comprises a glass material and a ceramic material in a combination or mixture.

"Density" means the ratio of mass to volume of an object. The unit of density is typically g/cm³. The density of an object can be calculated e.g. by determining its volume (e.g. by calculation or applying the Archimedes principle or method) and measuring its mass.

"Ambient conditions" mean the conditions which the inventive solution is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions are adjusted to about 23° C. and about 1013 mbar.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

DETAILED DESCRIPTION

Figure 1A:
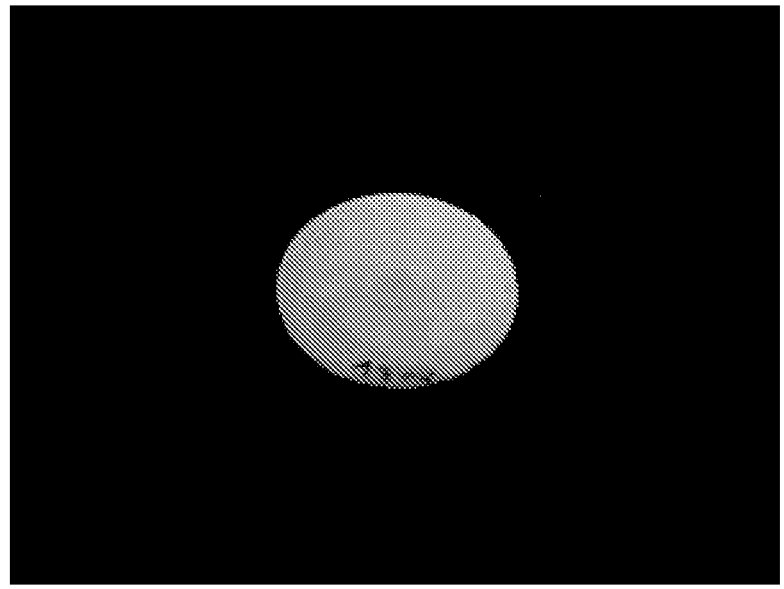
FIG. 1A shows a sintered zirconia disc illuminated from above.

In the dental field, water-based colouring liquids are commonly used for colouring especially zirconia based dental ceramic frameworks in a pre-sintered or porous stage. This is typically achieved by dipping the framework into a colouring solution in its entirety. By doing so, a homogenous colour of the whole dental ceramic is usually achieved.

However, if individual colouration or whitening in small defined areas is desired, the water-based liquids of the prior art cannot be used because the different colours typically will mix up and diffuse into parts of the ceramic article where they are not supposed to be present.

The inventive solution or composition solves this problem by allowing a dental technician to selectively apply a whitening agent to the surface of a dental ceramic e.g. using a brush.

It was found that the whitening agent remains on the spot or area of the surface where the composition has been applied to and does typically not diffuse through the rest of the material of the porous dental ceramic.

Thus, the invention enables the local and specific application of a whitening agent to selective parts of the surface of a ceramic material. It allows an exact whitening of individual parts of the surface of a dental ceramic. This may facilitate the imitation of white spots, which can sometimes be found on natural teeth.

The composition can also be used to apply an opaque surface layer to the inner and/or outer surface of a translucent dental ceramic, especially dental ceramic frameworks or dental monolithic ceramic restorations. In case of the framework being made of zirconia, the composition does not change the chemical composition of the material and does not diminish its beneficial properties.

The composition is typically applied to the surface of pre-sintered, porous dental ceramic. The painted features remain essentially sharp even if the bulk of the dental ceramic is still wet from a prior colouring step.

Thus, the inventive composition can also be applied to wetted dental ceramics, which have already been coloured by using a commercially available water-based colouring liquid, without the risk of the colour spreading indiscriminately due to diffusion.

On the other hand the inventive composition is also compatible with water-based colouring liquids in the sense that application of the composition will not affect the subjacent "background colour" of the dental ceramic having already been treated with a water-based colouring liquid in an undesired manner.

If desired, the whitening impression produced by the composition in the material can be further adjusted by diluting the composition with a dilution liquid or simply with more solvent.

Without wishing to be bound to a particular theory, a possible explanation for this finding is as follows:

If the composition is applied to a dry, porous material, it will migrate into the pores of the material. But this happens only to a very limited extent, mainly due to the comparably high viscosity of the composition. If the composition, however, is applied to a water-soaked, porous material, the water-soluble solvent will mix with the water already present inside the pores of the ceramic material. The whitening agent, however, will precipitate at higher pH values. If the mixing with the liquid already present in the pores raises the pH value far enough, precipitation will hold the whitening agent in place and minimize diffusion.

Thus, by mixing a (e.g. water-soluble or water-dispersible) whitening agent, an acid and a water-soluble liquid, which is able to take up, solve or stabilize the whitening agent in the liquid one or more of the above mentioned objective(s) (e.g. sufficiently high viscosity and/or pH-dependent precipitation behaviour) can be achieved.

The inventive composition can be used for selectively whitening the surface of dental ceramic(s), especially of wetted pre-sintered or porous dental ceramic(s).

Moreover, it was found that the inventive composition (s) remain stable over a considerable long period of time. They typically do not show visible (to the human eye) precipitation of the whitening agent during storage at ambient conditions (23° C., normal pressure).

Other embodiments, features and advantages of the present invention will be apparent from the following detailed description, drawings, and claims.

The composition is used for being selectively applied to parts of the surface of a dental ceramic. That is, the composition is only applied to parts of the surface of the dental ceramic but usually not to the whole surface. In contrast to commercially available colouring liquids, the dental ceramic is not dipped completely into the inventive composition.

Moreover, the composition cannot only be applied to dry surfaces of dental ceramics, but also to wetted dental ceramics, especially to pre-sintered or porous dental ceramics.

The inventive solution typically has an adequate viscosity so that a sufficient amount of composition can be applied to the surface of the dental ceramic.

According to one embodiment, the solution has a viscosity above about 10 or above about 50 or above about 100 mPa·s (measured at 23° C. with a shear rate of 50 s$^{-1}$). The viscosity of the solution is typically below about 10,000 or below about 5,000 or below about 2,000 mPa·s (measured at 23° C. with a shear rate of 50 s$^{-1}$).

Typical viscosity ranges include from about 10 to about 10,000 or from about 20 to about 8,000 or from about 50 to about 5,000 mPa·s (measured at 23° C. with a shear rate of 50 s$^{-1}$).

If the viscosity of the composition is too high, the whitening agent might not be able to enter the pores of the ceramic material at all. On the other hand, if the viscosity of the composition is too low, the whitening agent might diffuse through the pores too much.

If desired, the measurement of the viscosity can be done as follows: A viscosimeter MCR300 (from Anton Paar Comp.) is used. A portion of the composition is placed between two steel discs with a diameter of 8 mm and a gap of 1 mm at a temperature of 23° C. The gap is filled completely with the composition. Excess composition is removed. The shear rate between the rotating discs d(gamma)/dt is set constantly to 50 s$^{-1}$. The measurement is done 500 s after starting the shearing process of the composition.

Thus, the composition is typically in the form of a liquid which can be applied onto the surface of either a dry or wet, optionally pre-coloured, porous zirconia based dental ceramic.

If the porous zirconia is already wetted, the composition will solve into the geometry within minutes and disappear from the surface.

If the composition is used in excess, not all of it will migrate into the pores of the porous zirconia based material. The composition remaining on the surface can be wiped off, if desired, before or after sintering without problems.

If dissolved in water, the composition typically has a pH-value in the range of between about 0 to about 4.5 or about 0.5 to about 4. Measurement of the pH-value can be achieved by means known by the person skilled in art. E.g. an instrument like Metrohm™ 826 or pH indicator paper can be used.

For water-free compositions, the pH-value can be determined as follows: The composition may be mixed with a certain amount of water (e.g. 1:1) and the pH value measured in the above stated manner.

Providing an acidic solution can be beneficial in that the whitening agent can easier be dissolved in the composition. Whitening agents often tend to precipitate from the composition if the pH value is raised, e.g. above a value of 5 or 6 or 7.

In one embodiment the composition is transparent.

A composition can be characterized as transparent within the meaning of the invention if a beam of visible light (about 400 to about 700 nm) is not scattered by the solution and the solution does not appear to be turbid. Providing a transparent composition can be desirable in that the whitening agent being contained in the composition is either a real solution (e.g. dissociation into ions) or a dispersion (e.g. particle size smaller than wavelength of visible light).

The composition comprises a whitening agent which comprises components which agglomerate and/or precipitate if the composition is adjusted to a pH above 5 or above 5.5 or above 6 or above 6.5 or above 7.

If desired, agglomeration and/or precipitation of the components can be initiated by simply raising the pH value of the solution, e.g. by drop-wise adding a base like NaOH (e.g. 1 molar solution) to the composition and measuring the pH value.

If the composition was initially transparent, white clouds will appear in the composition indicating that the components started to agglomerate. The agglomeration can continue and finally result in a precipitation of the agglomerated components over time (e.g. after about 1 h).

As outlined above, the agglomeration might be caused by the formation of components being insoluble or hardly soluble within the liquid used.

The agglomeration and/or precipitation might also be caused by destabilizing the outer shell of solvent molecules surrounding and stabilizing e.g. nano-sized particles.

The components being contained in the whitening agent may include metal cations, nano-sized particles and mixtures thereof.

Examples of metal cations of the whitening agents include Zr, Ti and mixtures thereof.

It was found that it is often beneficial if the nature of the cations of the whitening agent is similar or identical to the atoms or cations forming the structure of the dental ceramic to be treated. By choosing this kind of cations, the crystal structure of the dental ceramic and thus its mechanical strength is typically not negatively affected during sintering. In contrast to this, choosing a different kind of cation may lead to a disruption of the crystal structure, inclusions, etc. during sintering, thus severely hampering the material's mechanical strength.

E.g. using silicon cations or silica containing whitening agent for zirconia based dental ceramics, may lead to a decrease in strength of the sintered dental ceramic by up to about 80%.

According to one embodiment, the whitening agent is water-soluble.

Using a water-soluble whitening agent can be beneficial in that it is easier to influence the solubility of the agent by adjusting the pH value of the composition itself or by application of the composition to a material infiltrated with a fluid of different pH value.

The whitening agent can comprise, essentially consist of or consist of a salt comprising metal cations and anions, wherein the anions are selected from the group consisting of $OH^-$, $NO_3^-$, $NO_2^-$, $CO_3^{2-}$, $HCO_3^-$, $ONC^-$, halogen anions (fluoride, chloride, bromide), acetates and mixtures thereof.

As described in more detail below, a complexing agent can be added as a separate component. However, it is also feasible that the complexing agent is at least partially identical with the anion of the whitening agent, or that the anion of the whitening agent can be classified as complexing agent as well.

Examples for these kinds of anions include gluturate, lactate, gluconate, propionate, butyrate, glucuronate, benzoate, phenolate, citrate, salicylate, glycinate, acetylacetonate, propylendiamine, ascorbate and others.

Besides or in addition to metal cations the whitening agents comprise nano-sized particles. Thus, the whitening agent comprises metal cations or nano-sized particles or a mixture of both (metal cations and nano-sized particles), wherein the presence of nano-sized particles can sometimes be preferred.

Nano-sized particles typically have a (hydrodynamic) diameter in the range from about 1 nm to about 500 nm or from about 2 nm to about 100 nm or from about 3 nm to about 20 nm. The diameter should be tailored to be compatible with (i.e. being smaller than) the pore size of the ceramic material to which the composition should be applied.

If desired, the (hydrodynamic) diameter of the particles can be determined by a dynamic light scattering method.

Dynamic Light Scattering (DLS) is an analytical method using the Brownian motion of particles in a solvent to determine their size. Basis of the method is that smaller particles move faster than bigger particles. A laser is used to irradiate a sample and the light scattered by the particles is detected. Small, fast moving particles cause quick fluctuations of the detected signal, while bigger and slower particles cause slower fluctuations.

The DLS method determines the so called "hydrodynamic diameter" of the dispersed particles. The moving particles possess a shell of solvent that moves along with them through the solution. The hydrodynamic diameter is the diameter of the solid particle plus the solvent shell. As a result, the actual particle is always smaller than the measured diameter.

A device which can be used for the DLS measurements is the Zetasizer™ Nano ZS (Malvern).

The nano-sized particles may comprise, essentially consist of or consist of $ZrO_2$ or $TiO_2$ particles, wherein $ZrO_2$ based substances are sometimes preferred.

The amount of whitening agent used is not particularly limited unless the result to be achieved cannot be obtained.

The metal ions are contained in the solution in an amount sufficient to achieve an adequate effect within the dental ceramic.

Good results can be achieved e.g. with amounts (calculated with respect to the metal) in the range of about 1 to about 20% by weight of whitening agent or in the range of about 3 to about 15% by weight, or in the range of about 4 to about 12% by weight with respect to the weight of the whole composition.

If the amount of whitening agent used is too low, the effects obtained in the ceramic might be too weak for the intended use.

If the amount of whitening agent used is too high, it can be difficult to produce a solution. So, there might remain large particles within the composition, which can cause undesired shading effects on the surface of the dental ceramic or influence other material properties.

The composition comprises a liquid. The liquid is miscible with water. The liquid, however, is not water.

Typically, the liquid can be characterized by at least one of the following features:
  molecular weight (Mw): from about 30 to about 1,000 g/mol or from about 60 to about 400 g/mol;
  viscosity: from about 1 to about 2,000 mPa·s or from about 100 to about 1,500 mPa·s or from about 200 to about 1,000 mPa·s (measured at 23° C. at a shear rate of 50 $s^{-1}$);
  free of polymerizable groups like (meth)acrylate groups, epoxy groups, carbon-carbon unsaturated groups;
  not containing elements like S, P.

Mw (substance) is the average molecular weight of the respective polymer used.

Liquids which can be used include polyalcohols including ethylene glycol, polyethylene glycols, glycerol and mixtures thereof.

Polyethylene glycols which can be used can be represented by formula (1)

$$R1O-(CH2-CH2-O)m\text{-}R1 \qquad (1)$$

with R1=H, Acyl, Alkyl, Aryl, Alkylaryl, Polypropylglycol, Poly-THF, preferably H, Acetyl, Methyl, Ethyl, Propyl, Butyl, Hexyl, Octyl, Nonyl, Decyl, Lauryl, Tridecyl, Myristyl, Palmityl, Stearyl, Oleyl, Allyl, Phenyl, p-Alkylphenyl, Polypropyleneglycol, Poly-THF and m=about 2 to about 100, preferably about 2 to about 20, more preferably about 2 to about 5

The average molecular weight (Mw) of the polyethylene glycol should be in the range of about 100 to about 5.000, preferably in the range of about 100 to about 1.000, more preferably in the range of about 100 to about 300.

If desired, the average molecular weight (Mw) can be determined according to procedures known to a person skilled in the art as described for example in Arndt/Müller, Polymercharakterisierung, Hanse Verlag, 1996. Depending on the molecular weight to be determined, it might be necessary to apply different measurement methods (see below).

Most PEGs (polyethylene glycols) include molecules with a distribution of molecular weights, i.e. they are polydisperse. The size distribution can be characterized statistically by its weight average molecular weight (Mw) and its number average molecular weight (Mn), the ratio of which is called the polydispersity index (Mw/Mn). Mw and Mn can be measured by mass spectroscopy.

Specific examples of water-miscible liquid, which can be used, include polyol(s) (including polyvinyl alcohol), glycol ether(s) (e.g., PEG 200, PEG 400, PEG 600, diethylene glycol methyl ether, diethylene glycol ethyl ether), alcohol(s) (including 1,2-propanediol, 1,3-propanediol, ethanol, (n- and iso-)propanol, glycerol), glycerol ether, and mixtures thereof.

In particular, the following liquids were found to be useful: glycerol, ethylene glycol, propylene glycol and mixtures thereof.

According to one embodiment, the liquid should be able to dissolve the whitening agent. Dissolving means that the composition does not contain particles being visible to the human eye.

The amount of liquid used is not particularly limited unless the result to be achieved cannot be obtained.

The liquid is typically used in an amount of at least about 20 or at least about 50 or at least about 70 wt.-% with respect to the whole weight of the solution.

There is no particular upper amount, however, the liquid is typically used up to an amount of up to about 98 or up to about 96 or up to about 90 wt.-% with respect to the whole weight of the composition.

Useful ranges for the liquid include from about 20 to about 98 wt.-% or from about 50 to about 96 wt.-% or from about 70 to about 90 wt.-% with respect to the whole weight of the composition.

Besides or in addition to a complexing agent, the composition may contain an acid.

The acid used may contain water or is essentially water-free but should be solvable in the liquid used.

Examples of acids which can be used include organic acids (like acetic acid, citric acid, malonic acid), inorganic acids (e.g. hydrochloric acid, nitric acid, sulfuric acid) and mixtures thereof, wherein the use of organic acids is sometimes preferred.

The acid is typically used in an amount that the pH value of the composition is below 5 or below 4.5 or below 4 or below 3.5 or below 3.

The acid is typically present in an amount of at least about 1 or at least about 5 or at least about 10 wt.-% with respect to the weight of the composition.

The acid is typically present in an amount of at most about 75 or at most about 50 or at most about 20 wt.-% with respect to the weight of the composition.

Typical ranges for the acid include from about 1 to about 75 or from about 5 to about 50 or from about 10 to about 20 wt.-% with respect to the weight of the composition.

If the amount of acid used is outside the above mentioned ranges, the components of the whitening agent might already start to agglomerate and to precipitate prior to use. This might negatively affect the storage stability.

According to one embodiment the composition contains water.

Water can be present in an amount from about 1 to about 60 wt.-% or from about 2 to about 50 wt.-% or from about 5 to about 20 wt.-% with respect to the weight of the whole composition.

According to another embodiment the composition is a non-water based composition.

Essentially free of water means that the composition does not contain water, which has been willfully added as a solvent. However, traces of water being present in the composition due to the components used are acceptable. Thus, this term includes that water might be present up to an amount of about 10 wt.-% or up to about 7 wt.-% or up to about 5 wt.-% or up to about 2 wt.-% or up to about 1 wt.-% with respect to the whole solution or composition, respectively.

Providing a non-water based composition can be beneficial in that the migration of the composition into the pores of the porous dental ceramic is further reduced. This can be especially useful, if the dental ceramic has already been treated with a water-based substance, e.g. a colouring solution. Another advantage is that the composition cannot dry out (given that the liquid used is high boiling), which is a major advantage regarding handling of the composition.

Besides or in addition to an acid, the composition may comprise a complexing agent.

The complexing agent is able to form a complex with the metal ions of the whitening agent. The complex formed is typically soluble in the liquid. The complex formed may be better soluble in the liquid than in water.

Typically, if present, the complexing agent is present in the composition in an amount sufficient to dissolve the whitening agent in the liquid or to prevent precipitation of the whitening agent.

The complexing agent can be present in an amount of at least about 1 wt.-% or at least about 5 wt.-% or at least about 10 wt.-% with respect to the amount of the whole composition. There is no upper limit, however, usually the amount of complexing agent used does not exceed an amount of about 50 wt.-% or about 40 wt.-% or about 30 wt.-% with respect to the amount of the whole composition.

E.g., the complexing agent can be used in an at least stoichiometric ratio with respect to the molar amount of the ions contained in the whitening agent.

Good results can be achieved, if the ratio of molar amount of complexing agent to the molar amount of metal ion being present in the whitening agent is equal to or greater than about 1 or about 2 or about 3.

If the amount of complexing agent used is too low, the whitening agent might not be dissolved entirely.

If the amount of complexing agent used is too high, the excess complexing agent itself might remain unsolved.

The complexing agent is usually added as a separate component of the composition. However, it can also be added as part of the whitening agent, e.g. as counter ion to the metal ion being present in the whitening agent. Examples include citrate, acetate and acetylacetonate.

Without wishing to be bound by any theory, it is assumed that the complexing agent is able to form a complex with the metal ion(s) of the whitening agent assisting the agent in dissolving in the chosen solvent and preventing the whitening agent from precipitating from the composition especially during storage.

The increased stability of a chelated complex is called the chelate effect. In this respect, the complexing agent can also be characterized as a chelating agent (or a polydentate ligand), which can bond to more than one coordination site on the central atom. Because it is necessary to break all of the bonds to the central atom for the ligand to be completely displaced, it requires more energy to increase the number of separate molecules. If a chelate were replaced by several monodentate ligands (such as water or ammonia), the total number of molecules would decrease, whereas if several monodentate ligands were replaced by a chelate, the number of free molecules increases. The effect is therefore entropic in that more sites are used by less ligands and this leaves more unbonded molecules: a total increase in the number of molecules in solution and a corresponding increase in entropy.

According to the present invention the complexing agents can be classified as follows:

Complexing agents with 6 coordinating ligands include EDTA (ethylene diamine tetra acetic acid); 18-crown-6;

2,2,2-crypatand; polymeric ligands like poly acrylate, poly asparagate, acidic peptides with an "infinite" number of coordinating ligands are counted as complexing agents with 6 coordinating ligands.

Complexing agents with 5 coordinating ligands include 15-crown-5; cyclo-pentadien.

Complexing agents with 4 coordinating ligands include NTA (nitrilotriacetate); 12-crown-4; triethylentetramine; porphin$^{2-}$; phthalocyanin$^{2-}$ bis(salicilate)ethylenbis(imin)salen$^{2-}$.

Complexing agents with 3 coordinating ligands include $C_3H_5O(COO)_3^{3-}$.

Complexing agents with 2 coordinating ligands include $HC_6H_5O_7^{2-}$; salicylate, glycinate; lactate; acetylacetonate; propylendiamine; ascorbate $C_6H_6O_6^{2-}$; $C_3H_5O(COOH)(COO)_2^{2-}$.

A citrate is an ionic form of citric acid, such as $C_3H_5(COO)_3^{3-}$, that is, citric acid minus three hydrogen ions. Citrates are compounds containing this group, either ionic compounds, the salts, or analogous covalent compounds, esters. Since citric acid is a tribasic acid, intermediate ions exist, hydrogen citrate ion, $HC_6H_5O_7^{2-}$ and dihydrogen citrate ion, $H_2C_6H_5O_7^-$. These may form salts as well, called acid salts. Salts of the hydrogen citrate ions are weakly acidic, while salts of the citrate ion itself (with an inert cation such as sodium ion) are weakly basic.

Complexing agents having anionic groups as complexing ligands can be preferred. At least parts of the complexing ligands should be anionic. Complexing agents having only uncharged complexing ligands (or even cationic ligands) like pure amines (e.g. ethylendiamin at pH values at 8 to 14) might not yield sufficiently stable solutions.

The inventive solution may also contain one or more additive(s).

Additives which can be added to the composition include stabilizers (such as methoxy phenol hydrochinone, Topanol A, ascorbic acid and mixtures thereof), buffers (such as acetate or amino buffers and mixtures thereof), preservative agents (such as sorbic acid or benzoic acid and mixtures thereof), soluble colourants (e.g. colourants which can be added to food) and mixtures thereof.

Adding soluble colourants can be beneficial in order to enhance the visibility of the composition during use, especially, if the composition is transparent. Thus, the practitioner can easily determine to which parts of the surface of the dental ceramic the composition has already been applied and which parts have not been treated yet and should remain untreated. On the other hand the soluble colourants which are typically of organic nature will be burnt during a later sintering step and thus not be incorporated into the crystal structure of the dental ceramic.

Examples of soluble colourants which can be used include Riboflavin (E101), Ponceau 4R (E124), Green S (E142).

There is no need for additive(s) to be present, however, if they are present, they are typically present in an amount which is not detrimental to the purpose to be achieved when applying the composition.

If additive(s) are present, they are typically present in an amount of about 0.01 to about 10 wt.-% or from about 0.05 to about 5 wt.-% or from about 0.1 to about 3 wt.-% with respect to the whole composition.

According to a further embodiment, the composition comprises the components in the following amount:

the liquid in an amount of about 20 to about 98 wt.-% or from about 70 to about 95 wt.-%, the whitening agent in an amount of about 1.0 to about 20 wt.-% or from about 3.0 to about 15 wt.-% (calculated with respect to the amount of metal contained therein), the acid and/or complexing agent in an amount of about 1 to about 75 wt.-% or from about 5 to about 50 wt.-% optionally additives in an amount of about 0 to about 10 wt.-% or from about 0.05 to about 5 wt.-%, wt.-% with respect to the whole composition.

The composition can be produced by mixing its components. This can be done at room temperature or by applying heat and/or while stirring. The pH value can be adjusted as needed.

Applying heat and/or stirring can be beneficial in order to accelerate the dissolution process of the whitening agent into the solvent.

The composition is typically stirred until the whitening agent and the acid are completely dissolved or dispersed in the liquid (e.g. from about 5 min to about 24 h). During this step, the formation of nano-sized particles can take place.

Undesired precipitations can be removed by filtering, if desired.

If desired, additives (like those mentioned above) can be added.

The dental ceramic to which the composition is to be applied is porous. Moreover, the dental ceramic typically has an outer and an inner surface. The outer surface typically has an overall convex shape, whereas the inner surface typically has an overall concave shape.

The dental ceramic onto which the solution is applied can be dry or wet.

"Wet" means that the ceramic material still contains a small amount of water. However, there should be no visible spots of water residues on the surface.

A pre-sintered or porous material sample is considered wet, if the material has been completely dipped into water for about 10 s, removed from the water and wrapped for about 10 s into a paper tissue being able to absorb water or alternatively, if a water-based solution has been applied to large areas of the material using e.g. a sponge, a brush, etc.

The surface of a pre-sintered or porous material sample is considered dry, if the material has been completely dipped into a water-based solution for about 10 s, removed from the water, wrapped for about 10 s into a paper tissue being able to absorb water and placed into an oven for about 1 h at a temperature of about 200° C. or left to dry open to the air for about 4 h, or if no water-based solution has been applied to the pre-sintered or porous ceramic at all.

If desired, the dental ceramic can be pre-coloured using colouring solutions which are already known in the art.

If the colouring solution, which provide a background colour to the dental ceramic, possess a pH value above 5, the colouring solution will facilitate precipitation of the whitening agent being contained in the composition shortly after entering the porous material and fix it to the intended position.

It was found that using the inventive composition in combination with slightly basic colouring liquids (e.g. pH-value from about 8 to about 12) often gives even better results.

On the other hand, using acidic colouring liquids (e.g. pH-value from about 6 to about 1) in combination with the inventive composition may increase the solubility of the whitening agent and facilitate the diffusion of the whitening agent into the pores of the dental ceramic, having the effect that the whitening effect is not as precise as the whitening effect which can be achieved with the combination outlined above. However, an opacifying effect can still be achieved.

The dental ceramic to which the composition is applied is porous and thus absorbent. Porous dental ceramics can be obtained e.g. by pre-sintering a compressed ceramic powder.

The composition of the present invention is applied to the surface of a porous dental ceramic bodies of various compositions, especially such comprising or preferably consisting essentially of $ZrO_2$ and/or $Al_2O_3$, respectively.

The term "consisting essentially of" means that the major part (e.g. greater than about 80 or about 85 or about 90 wt.-%) of the dental ceramic is based on either $ZrO_2$ or $Al_2O_3$ or a mixture of these oxides. The rest of may be comprised of oxides selected from $HfO_2$ and stabilizers including $Y_2O_3$, CaO, MgO, $CeO_2$ or mixtures thereof.

These compositions are known to the skilled person in the art (examples of useful compositions are described e.g. in WO 00/4618 A1).

Other ceramic materials which can be used are described in U.S. application No. 61/545,243 filed Oct. 10, 2011.

The ceramic materials described in that application are often highly translucent and are prepared by using a sol/gel process. Especially in combination with those highly translucent materials the inventive process and composition described in the present text can be beneficial.

According to one embodiment, the dental ceramic is a $ZrO_2$ based ceramic and is preferably stabilized with $Y_2O_3$. The dental ceramic is in a pre-sintered and/or porous stage.

Yttrium doped tetragonal stabilized zirconia is sometimes also referred to as YTZP and commercially available from e.g. Tosoh Comp., Japan.

Selectively applying the composition to the surface of the dental ceramic is usually achieved by painting e.g. using a brush. However, the composition can also be applied by using a sponge or fabric or by spraying.

Drying the treated dental ceramic is not absolutely necessary, but can be preferred to reduce the time needed for firing and to avoid undesired in-homogenous colour effects. Drying can be effected by simply storing the dental ceramic e.g. on a plate at ambient conditions for a couple of hours (about 1 to about 3 h). If, however, a high boiling solvent is used, drying might be difficult to achieve.

The firing conditions are dependent on the ceramic material used. A furnace which can be used is the commercially available LAVA™ Therm (3M ESPE). During the firing process the coloured dental ceramic is sintered to its final shape, thereby undergoing changes with regard to dimension, density, hardness, raw breaking resistance and/or grain size.

The firing usually takes place for a $ZrO_2$ based ceramic at a temperature above about 1300° C., preferably above about 1400° C., more preferably above about 1450° C. and lasts for at least about 0.5 h, preferably for at least about 1 h, more preferably for at least about 2 h.

For an $Al_2O_3$ based ceramic the firing usually takes place at a temperature above about 1350° C., preferably above about 1450° C., more preferably above about 1650° C. and lasts for at least about 0.5 h, preferably for at least about 1 h, more preferably for at least about 2 h.

The invention is also related to a dental ceramic obtainable by a process as described in the present text. A dental ceramic having being treated according to the above described process steps is different from dental ceramics which have been treated with essentially water-based colouring or whitening solutions. Applying water-based colouring or whitening solutions to the surface of dental ceramics typically leads to diffuse colouring or whitening of the whole dental ceramic, whereas the inventive composition allows for a more accurate, well defined whitening effect.

If desired, the extent of diffusion of the composition on the surface of the treated dental ceramic can be determined as follows:

The width of a line drawn with the inventive composition can be visually confirmed after sintering. More accurately, X-ray fluorescence (XRF) measurements can be conducted in micro mapping mode to determine the line's width, i.e. scanning the surface of the ceramic in e.g. 0.25 mm steps and measuring only small spots of e.g. about 0.5 mm diameter.

A width of e.g. about 0.5 mm of the drawn structures is considered to meet the expectations of a dental technician in most cases for an effect agent being applied to only selective parts of the surface of a dental ceramic.

The dental ceramic can have the shape of a crown, inlay, onlay, veneer, facing, abutment, bridge or framework for a crown or bridge.

According to a further embodiment, the invention is directed to a kit of parts comprising
at least one receptacle containing the composition as described in the present text;
one receptacle containing the liquid as described in the present text; and
optionally at least one receptacle containing a colouring liquid,
optionally application and mixing appliances.

Examples of receptacles include bottles, wells, tubes and vessels.

A typical example of a kit according to the invention includes about 2 to 10 receptacles containing a) the composition as described in the present text, b) a separate receptacle containing only the liquid contained in the composition, c) one or more receptacles containing colouring solutions each differing from the others by its content and/or concentration of colouring metal ions.

Colouring liquids for dental ceramics are meanwhile well known in the art. Examples of colouring solutions are described in U.S. Pat. No. 6,709,694, US 2006/0117989, WO 2009/014903, EP application No. 11177189. The content of these references is herewith incorporated by reference. Theses colouring liquids typically comprise water, metal cations selected from rare earth elements, transition metal and mixtures thereof, and sometimes a complexing agent or further additives like (poly)ethylene glycol. The colouring liquids are typically used for homogeneously colouring dental ceramics and in particular porous dental ceramic framework.

The liquid being provided in a separate receptacle enables the practitioner to further individualize or dilute the composition, especially with respect to its intensity.

Examples of application appliances include brushes, sponges, (hollow) needles, etc.

Examples of mixing appliances include mixing wells, trays, plates, slides, etc.

The composition of the invention does typically not contain components which might produce a toxic, injurious, or immunological response in living tissue or components or additives which jeopardize the intended purpose to be achieved with the present invention, especially in the sintered ceramic.

Thus, for examples components or additives added in an amount which finally (e.g. after a sintering step) results in a non-tooth-coloured article are usually not contained in the final dental restoration. Typically, an article is characterized as tooth coloured if it can be allocated a colour from the Vita™ colour code system, known to the person skilled in the art.

Moreover, if possible, the composition should not or only contain a small amount of ingredients which can be detrimental to the firing equipment during the sintering process.

According to a specific embodiment, the inventive solution does not contain reactive organic monomers (i.e. chemically reactive moieties like double bonds, e.g. (meth)acrylates). Thus, after preparation, the composition does not exhibit chemical reactivity under ambient conditions, i.e. components being present in the composition do not react with each other at ambient conditions.

The complete disclosures of the patents, patent documents, and publications cited herein are incorporated by reference in their entirety as if each were individually incorporated.

The following examples are given to illustrate, but not limit, the scope of this invention.

EXAMPLES

Unless otherwise indicated, all parts and percentages are on a weight basis, all water is deionized water, and all molecular weights are weight average molecular weight. Moreover, unless otherwise indicated all experiments were conducted at ambient conditions (23° C.; 1013 mbar).

Materials Used

Porous pre-sintered zirconia: Lava™ Frame zirconia (3M ESPE)—lot#: 396539.

Wet porous pre-sintered zirconia: Lava™ Frame zirconia (3M ESPE)—lot#: 396539 dipped for 120 s into de-ionized water.

Colouring Liquid (A): de-ionized water (about 90 wt.-%, triammonium citrate (about 4 wt.-%), poly(ethylene) glycol (about 2 wt.-%) and a mixture of praseodymium acetate, erbium acetate and manganese chloride hydrate (about 4 wt.-%), pH value 7-8.

Colouring Liquid (B): de-ionized water (about 89 wt.-%), hydrochloric acid (<1 wt.-%), poly(ethylene)glycol (about 6 wt.-%) and a mixture of iron, erbium and manganese chloride hydrates (about 4 wt.-%), pH value 1.

Inventive Example 1

5.0 g of glycerol were mixed with 10.0 g of acetic acid (32 wt.-%) and 6.0 g of zirconium(IV) acetate hydroxide by stirring for about 1 h or until a clear solution with a pH value of about 3 was obtained. DLS-measurement of this solution revealed a hydrodynamic diameter of the particles in the range of 6 to 11 nm.

The mixture was applied to a dry disc of porous pre-sintered Lava™ Frame zirconia (3M ESPE). Smaller and bigger spots were painted onto the surface. The solution was absorbed into the zirconia structure. This procedure was repeated with wetted discs, infiltrated with de-ionized water, colouring liquid (A) and colouring liquid (B), respectively.

Figure 1B:
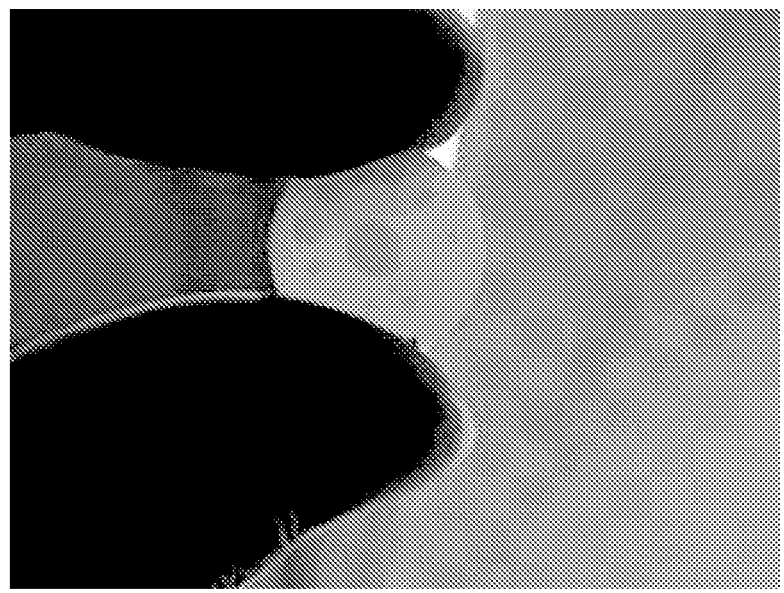
FIG. 1B shows a sintered zirconia disc illuminated from behind.

After that, the material was put into a Lava™ Therm furnace (3M ESPE) and sintered at about 1500° C. for 2 h. As a result, dense zirconia discs were obtained (results see table below, picture of the sintered disc which was painted in dry state see FIGS. 1A and 1B).

Inventive Example 2

Water-Free 5.0 g of ethylene glycol were mixed with 0.75 g of acetic acid (100%) and 0.75 g of zirconium(IV) acetate hydroxide by stirring for about 4 h until a clear solution with a pH value of about 3 was obtained.

The mixture was applied to a dry disc of porous pre-sintered Lava™ Frame zirconia (3M ESPE). Smaller and bigger spots were painted onto the surface. The solution was absorbed into the zirconia structure. This procedure was repeated with wetted discs, infiltrated with deionized water, colouring liquid (A) and colouring liquid (B), respectively.

After that, the material was put into a Lava™ Therm furnace (3M ESPE) and sintered at about 1500° C. for 2 h. As a result, dense zirconia discs were obtained. The whitening/opacifying effect, however, was weaker than in Example 1 (results see Table below).

Comparative Example 10.00 g of de-ionized water, 0.20 g of triammonium citrate and 2.00 g of aluminium(III) chloride were mixed by stirring for a few minutes. A clear liquid with low viscosity was obtained.

The mixture was applied to one dry and to three wetted discs of porous pre-sintered zirconia. One of the wetted discs was produced by dipping a dry disc into de-ionized water, the other two by dipping a dry disc into a model colouring liquid (A) and (B), respectively.

For the painting process, there should be no free liquid from the soaking step remaining on the disc's surface.

Smaller and bigger spots were painted onto the surfaces, but the composition did not remain in shape and spread readily over all the discs instead. The painted features could not be seen shortly after painting anymore.

After that, the zirconia discs were put into a Lava™ Therm furnace and sintered at 1500° C. for 2 h.

As a result, dense zirconia discs were obtained. The painted spots, however, could not be seen, although a highly concentrated alumina solution was used. Only in the case of the disc infiltrated with colouring liquid (B) a very weak whitening effect could be observed, which might be attributed to the dilution of colouring liquid (B) where the composition was applied.

Results

| Example | painted in dry state | painted in wet state (infiltrated with de-ionized water) | painted in wet state (infiltrated with basic colouring liquid) | painted in wet state (infiltrated with acidic colouring liquid) |
| --- | --- | --- | --- | --- |
| I.E. 1 | **/+++ | − | **/+++ | +++ |
| I.E. 2 | */++ | − | */++ | ++ |
| C.E. 1 | − | − | − | + |

Described is the visibility of white spots, lines etc. painted on the surface of the samples if examined by a dental technician.
"+" indicates visibility of a whitening effect, i.e. the colour from the colouring liquids is reversed to white without increasing the opacity of the material.
"++" indicates good visibility of a whitening effect, i.e. the colour from the colouring liquids is reversed to white without increasing the opacity of the material
"+++" indicates very good visibility of a whitening effect, i.e. the colour from the colouring liquids is reversed to white without increasing the opacity of the material.
"*" indicates good visibility of an opacifying effect, i.e. there are white, opaque spots on the sample.
"**" indicates very very good visibility of an opacifying effect, i.e. there are white, opaque spots on the sample.
"−" indicates no visible effect.

The invention claimed is:

1. A process of selectively treating parts of the surface of a porous dental ceramic comprising the steps of
   a) providing a composition and a porous dental ceramic having an outer surface,
   b) applying the composition to only a part of the outer surface of the porous dental ceramic,
   c) optionally drying the porous dental ceramic, and
   d) optionally firing the porous dental ceramic,
   wherein the composition comprises
      a liquid being miscible with water, but not being water,
      a whitening agent comprising nano-sized metal oxide particles, metal ion containing components or mixtures thereof which precipitate if the composition is adjusted to a pH above 5,
      acid, complexing agent or mixture thereof.

2. The process according to claim 1, wherein the porous dental ceramic comprises $ZrO_2$, $Al_2O_3$, or mixtures of either of these oxides with the other.

3. The process according to claim 1, wherein the whitening agent comprises nano-sized particles having a diameter from about 1 nm to about 500 nm.

4. The process according to claim 1, wherein the porous dental ceramic fulfills at least one of the following conditions:
   i) the porous dental ceramic is in a porous and/or pre-sintered stage before the composition is applied,
   ii) the outer surface of the dental ceramic is wet before the composition is applied,
   iii) the porous dental ceramic of step a) has been treated with a solution having a pH-value above 5.

5. The process according to claim 1, the composition being essentially free of either of the following components:
   filler,
   colouring ions selected from iron, erbium, manganese, praseodymium or mixtures thereof,
   reactive organic monomers, and combinations thereof.

6. The process according to claim 1, the metal cations of the whitening agent comprising cations selected from Zr, Ti and mixtures thereof.

7. The process according to claim 1, the liquid being selected from the group consisting of polyol(s), glycol ether(s), glycerol ether(s), alcohol(s) and mixtures thereof.

8. The process according to claim 1, the composition being characterized by at least one of the following features: viscosity: from about 10 mPa*s to about 10,000 at 23° C., if dissolved or dispersed in water: pH-value in the range of between about 1 to about 4.5,
   being transparent to visible light.

9. The process according to claim 1, the whitening agent comprising anions, wherein the anions are selected from the group consisting of $OH^-$, $OAc^-$, $NO_3^-$, $NO_2^-$, $CO_3^{2-}$, $HCO_3^-$, $ONC^-$, $SCN^-$, $SO_4^2$, $SO_3^{2-}$, halogen anions and mixtures thereof.

10. The process according to claim 1, the composition comprising as complexing agent or acid a compound being selected from the group consisting of acetylacetonate, crown ethers, cryptands, ethylenediaminetriacetate and its salts, ethylenediaminetetraacetate (EDTA) and its salts, nitrilotriacetate (NTA) and its salts, citric acid and its salts, triethylentetramine, porphin, poly acrylate, poly asparagate, acidic peptides, phthalocyanin, salicylate, glycinate, lactate, propylendiamine, ascorbate, oxalic acid and its salts, acetic acid and its salts and mixtures thereof.

11. The process according to claim 1, the composition comprising
   a. the liquid in an amount of about 20 to about 98 wt.-%,
   b. the metal oxide or metal ion containing components of the whitening agent in an amount of about 1.0 to about 20 wt.-%,
   c. the acid, complexing agent or mixture thereof in an amount of about 1 to about 75 wt.-%, and
   d. optionally additives in an amount of about 0 to about 10 wt.-%,
   wt.-% with respect to the whole composition.

12. A dental ceramic article obtainable by a process as described in claim 1, the dental ceramic preferably having the shape of a crown, inlay, onlay, veneer, abutment, bridge, or framework for a crown or bridge.

13. Kit of parts comprising
   at least one receptacle containing the composition as described in claim 1;
   at least one receptacle containing a colouring liquid,
   optionally a receptacle containing the liquid contained in the composition,
   optionally application and mixing appliances.

14. A method of using the composition of claim 1 comprising selectively treating parts of the outer surface of a porous dental ceramic with the composition.

* * * * *

UNITED STATES PATENT AND TRADEMARK OFFICE
CERTIFICATE OF CORRECTION

PATENT NO. : 9,725,370 B2  
APPLICATION NO. : 14/351964  
DATED : August 8, 2017  
INVENTOR(S) : Michael Jahns Page 1 of 1

It is certified that error appears in the above-identified patent and that said Letters Patent is hereby corrected as shown below:

In the Specification

Column 1
Line 10 (approx.), delete "371 PCT/US 2012/062361," and insert -- 371 of PCT/US2012/062361, --.

Column 10
Line 46, after "5" insert -- . --.

Column 13
Line 1, delete "crypatand;" and insert -- cryptand; --, therefor.
Lines 8-9, delete "triethylentetramine;" and insert -- triethylenetetramine; --, therefor.
Line 9, delete "(salicilate)" and insert -- (salicylate) --, therefor.

Column 18
Line 65 (approx.), delete "very very" and insert -- very --, therefor.

In the Claims

Column 20
Lines 15-16 (approx.), in Claim 10, delete "triethylentetramine," and insert -- triethylenetetramine, --, therefor.

Signed and Sealed this  
Twenty-seventh Day of February, 2018

Andrei Iancu  
*Director of the United States Patent and Trademark Office*